United States Patent [19]

Sakurai et al.

[11] 4,342,708
[45] Aug. 3, 1982

[54] HYDROCARBON-SOLUBLE DIORGANOMAGNESIUM COMPOUNDS, HYDROCARBON SOLUTIONS CONTAINING THE SAME AND PROCESSES FOR PREPARATION THEREOF

[75] Inventors: Hisaya Sakurai; Yoshihiko Katayama; Tadashi Ikegami; Shigeo Tsuyama, all of Kurashiki, Japan

[73] Assignee: Asahi Kasei Kogyo Kabushiki Kaisha, Osaka, Japan

[21] Appl. No.: 169,233

[22] Filed: Jul. 16, 1980

[30] Foreign Application Priority Data

Aug. 9, 1979 [JP] Japan .................................. 54-101538

[51] Int. Cl.$^3$ .............................................. C07F 3/02
[52] U.S. Cl. ............................ 260/665 R; 252/431 R
[58] Field of Search ..................................... 260/665 R

[56] References Cited
U.S. PATENT DOCUMENTS 3,646,231 2/1972 Kamienski et al. ............. 260/665 R
3,755,478 8/1973 Kamienski ...................... 260/665 R
3,766,280 10/1973 Kamienski et al. ............. 260/665 R
4,069,267 1/1978 Kamienski et al. ............. 260/665 R
4,127,507 11/1978 Fannin et al. ................ 260/665 R X
4,222,969 9/1980 Fannin et al. ................... 260/665 R Primary Examiner—Helen M. S. Sneed
Attorney, Agent, or Firm—Sprung, Horn, Kramer & Woods

[57] ABSTRACT

Novel hydrocarbon-soluble isopropyl group-containing diorganomagnesium compounds and hydrocarbon solutions thereof are disclosed. The compound of the present invention has a high weight percent of Mg per one mol thereof, and the hydrocarbon solution of the present invention has a very low viscosity as compared with the conventional solutions. The hydrocarbon solution of the present invention can be prepared according any of various processes. If the reaction is carried out in an ether medium, the ether is substituted with a hydrocarbon solvent by removing the ether from the reaction mixture by distillation in the presence of the hydrocarbon solvent.

10 Claims, No Drawings

HYDROCARBON-SOLUBLE DIORGANOMAGNESIUM COMPOUNDS, HYDROCARBON SOLUTIONS CONTAINING THE SAME AND PROCESSES FOR PREPARATION THEREOF

The present invention relates to novel hydrocarbon-soluble diorganomagnesium compounds, hydrocarbon solutions containing the same and processes for the preparation thereof. More particularly, the present invention relates to novel isopropyl group-containing dialkylmagnesium compounds, hydrocarbon solutions containing the same, and processes for the preparation thereof.

Organomagnesium compounds have a wide variety of uses, for example, they are useful not only as starting materials for the synthesis of various organometallic compounds and organic compounds but also as catalysts. The so-called Grignard reagents, which are synthesized in the medium of an ether, are especially well known. An organomagnesium compound may be used as a catalyst for the polymerization of vinyl monomers or as the starting material of a catalyst for the polymerization of olefins according to a Ziegler process. In this connection, it is noted that the presence of a polar compound such as an ether is not preferred in these polymerization systems, because the solvated forms of the organomagnasium compound and of a Ziegler type catalyst prepared therefrom which forms are formed in the ether medium are less effective as the catalysts. Further, the use of the ether is particularly undesirable due to considerations of flammability and explosibility. Therefore, the use of a solution of an organomagnesium compound dissolved in an inert hydrocarbon medium is desired. However, generally, organomagnesium compounds are insoluble or hardly soluble in hydrocarbon media. Therefore, it is difficult to obtain hydrocarbon solutions of conventional organomagnesium compounds. It is especially difficult to form hydrocarbon solutions of dialkylmagnesium compounds which have a small number of carbon atoms and are free of electronegative groups such as alkoxy groups, unless those compounds are formed into complexes with an organoaluminum or organozinc compound. Accordingly, various researches have been made with a view to searching for useful dialkylmagnesium compounds soluble in hydrocarbons, and dialkylmagnesium compounds as disclosed in U.S. Pat. Nos. 3,646,231, 3,766,280, 4,069,267 and 4,127,507 have been proposed as hydrocarbon-soluble ones. The former three patents disclose several compounds such as (sec-$C_4H_9$)$_2$Mg, an (iso-$C_4H_9$)$_2$Mg-(sec-$C_4H_9$)$_2$Mg complex, ($CH_3$)Mg(iso-$C_4H_9$), and a (sec-$C_4H_9$)Mg(n-$C_4H_9$)-(n-$C_8H_{17}$)$_2$Mg complex, and the last patent discloses compositions of (n-$C_4H_9$)$_2$Mg-($C_2H_5$)$_2$Mg. Hydrocarbon solutions of these dialkylmagnesium compounds inherently involve respective problems, the solution of which has been ardently desired. For example, in (sec-$C_4H_9$)$_2$Mg or the like, the weight percent of Mg per one mol of the compound is small since both the alkyl groups are large butyl groups providing a large molecular weight. On the other hand, in ($CH_3$)Mg(iso-$C_4H_9$) or the compositions of (n-$C_4H_9$)$_2$Mg-($C_2H_5$)$_2$Mg, the weight percent of Mg per one mol thereof is large but the viscosity of a hydrocarbon solution thereof is so high that difficulties may be encountered in handling and transferring of the solution on an industrial scale. In the case of the compositions of (n-$C_4H_9$)$_2$Mg-($C_2H_5$)$_2$Mg, a low-boiling-point compound such as $C_2H_5Cl$ should inevitably be used as the starting material and, in this sense, the preparation of the compositions on an industrial scale is disadvantageous.

We have made researches with a view to solving these problems. As a result, we have found novel hydrocarbon-soluble diorganomagnesium compounds and completed the present invention.

More specifically, in accordance with one aspect of the present invention, there is provided a hydrocarbon-soluble isopropylmagnesium compound having the general formula:

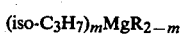

$$(\text{iso-}C_3H_7)_m MgR_{2-m}$$

wherein m is a number in the range of the formula $0.4 \leq m \leq 1.6$ and R represents a member selected from the group consisting of n-$C_4H_9$, n-$C_3H_7$, $C_2H_5$ and combinations thereof.

In accordance with another aspect of the present invention, there is provided a hydrocarbon solution comprising (a) an isopropylmagnesium compound as described above, and (b) a hydrocarbon solvent selected from the group consisting of aliphatic, cycloaliphatic and aromatic hydrocarbons, and mixtures thereof.

In the isopropyl group-containing dialkylmagnesium compound (iso-$C_3H_7$)$_m$Mg$R_{2-m}$ of the present invention, since the alkyl groups are smaller on the average than those in the aforementioned known (sec-$C_4H_9$)$_2$Mg or the like, the weight percent of Mg per one mol of the compound is higher. Furthermore, the viscosity of a hydrocarbon solution of the dialkylmagnesium compound of the present invention is lower than that of a hydrocarbon solution of the (n-$C_4H_9$)$_2$Mg-($C_2H_5$)$_2$Mg composition. Accordingly, the compound of the present invention is very advantageous in easy handling and transferring of the hydrocarbon solution thereof on an industrial scale. For example, the viscosity of a hydrocarbon solution of (iso-$C_3H_7$)Mg(n-$C_4H_9$) prepared according to the process (a) or (a') described hereinafter advantageously is about a tenth the viscosity of a hydrocarbon solution of a 1/1 composition of (n-$C_4H_9$)$_2$Mg-($C_2H_5$)$_2$Mg at the same molar concentration. More specifically, at a magnesium concentration of 0.5 mol/liter, the viscosity of a n-heptane solution of the former is lower than 1 centipoise at room temperature, while the viscosity of a n-heptane solution of the latter is higher than 10 centipoises at room temperature. Moreover, for the preparation of a hydrocarbon solution of a dialkylmagnesium compound according to the present invention, the use of $C_2H_5Cl$ which has a low boiling point and is difficult in handling can be avoided, and iso-$C_3H_7Cl$ or iso-$C_3H_7Br$ which is liquid at room temperature and easy in handling can be used. Accordingly, the hydrocarbon solution of the present invention can advantageously be prepared with ease. The solubility of, for example, (iso-$C_3H_7$)Mg(n-$C_4H_9$) of the present invention in a hydrocarbon is much higher than those of other asymmetric di(straight chain)alkylmagnesium compounds such as (n-$C_3H_7$)Mg(n-$C_4H_9$), and, hence, a high concentration hydrocarbon solution having an Mg concentration higher than 0.2 mol/liter can easily be obtained in the case of the dialkylmagnesium compound of the present invention.

None of the above-mentioned four U.S. patents disclose a hydrocarbon solution containing an isopropyl group-containing dialkylmagnesium compound according to the present invention. It is quite surprising that isopropyl group-containing dialkylmagnesium compounds as specified in the present invention are soluble in hydrocarbons and capable of being formed into solutions which are industrially advantageous.

The hydrocarbon solution according to the present invention will now be described in detail.

The solution of the present invention is a hydrocarbon solution containing an isopropyl group-containing dialkylmagnesium compound which is represented by the general formula (iso-$C_3H_7$)$_m$Mg$R_{2-m}$ wherein m is a number in the range of the formula $0.4 \leq m \leq 1.6$, preferably $0.9 \leq m \leq 1.1$, and R represents a member selected from the group consisting of n-$C_4H_9$, n-$C_3H_7$, $C_2H_5$ and combinations thereof, particularly preferably n-$C_4H_9$. Dialkylmagnesium compounds of the above general formula wherein m is 1 are particularly preferred. The formula $0.4 \leq m \leq 1.6$ means that the dialkylmagnesium compound of the present invention contains, on the average, 0.4 to 1.6 per molecule of isopropyl groups and 0.4 to 1.6 per molecule of the other specified alkyl groups which may be a combination of two or three kinds of specified alkyl groups. As the hydrocarbon solvent, there can be mentioned aliphatic hydrocarbons such as n-pentane, isopentane, n-hexane, n-heptane, n-octane, isooctane and pentamethylheptane; aromatic hydrocarbons such as benzene, toluene, xylenes, ethylbenzene, and α-methylnaphthalene; and cycloaliphatic hydrocarbons such as cyclohexane, methylcyclohexane, methylcyclopentane, cycloheptane, and cyclooctane. They may be either alone or in mixture. Aliphatic hydrocarbons, cycloaliphatic hydrocarbons and mixtures thereof are usually preferred. The Mg concentration in the hydrocarbon solution according to the present invention is not particularly critical, but it is preferred from the viewpoint of easiness in handling on an industrial scale that the Mg concentration be 0.01 to 3 mols/liter, especially 0.05 to 2 mols/liter. Such a concentration can easily be obtained by appropriately controlling the concentration of starting materials for the intended synthesis or by concentrating or diluting a solution obtained by the synthesis.

The process for the preparation of a hydrocarbon solution of an isopropyl group-containing dialkylmagnesium compound (iso-$C_3H_7$)$_m$Mg$R_{2-m}$ according to the present invention will now be described.

Any of various processes described below can be used for the preparation of the solution of the present invention. These processes will hereinafter be described in detail mainly with reference to an embodiment for the preparation of a compound wherein m is 1. Also in embodiments for the preparation of compounds wherein m is not 1, the intended solutions can be prepared in a similar manner to that in the embodiment for the preparation of the compound wherein m is 1. For example, as illustrated in Examples 2 through 5, 12 and 14 through 17, a mixture of two alkyl halides or two alkyl lithium compounds differing in alkyl may be used as the starting material or reactant to form an isopropyl group-containing dialkyl-magnesium compound wherein m is not 1.

(a) 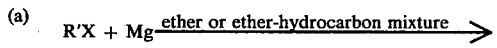

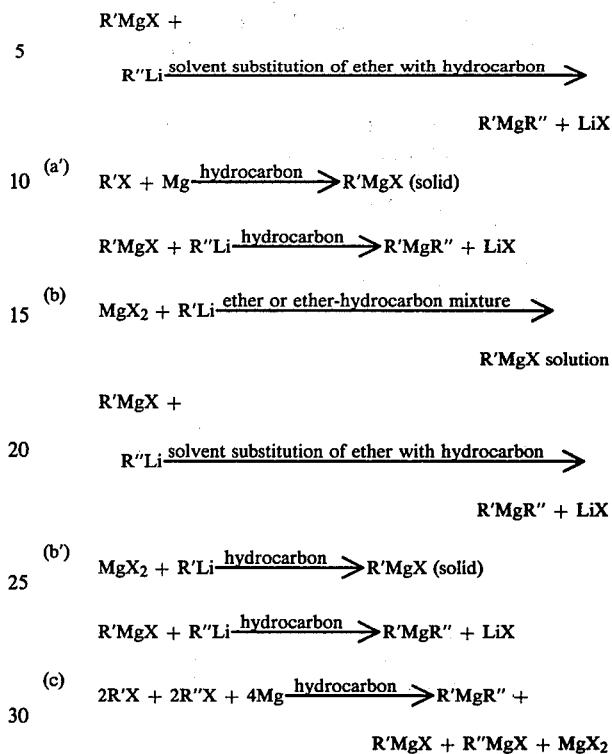

In the above-mentioned formulae, R' and R" each independently stands for alkyl and X stands for halogen. Of the foregoing processes, the processes (a), (a') and (c) are preferred from the viewpoints of easiness in carrying out the reaction and high reaction yield. These processes (a), (a') and (c) will now be explained one by one.

Process (a):

The starting materials to be used in the process (a) are as follows. Metallic magnesium used for the ordinary synthesis of Grignard reagents may be used. It may be in the form of either shavings or a powder. The use of a fine metallic magnesium powder of about 100 mesh in size or metallic magnesium activated with, for example, iodine according to a known method is especially preferred. As the alkyl halide reactant, there can be mentioned alkyl chlorides, alkyl bromides, alkyl iodides and mixtures thereof. Preferred are alkyl chlorides, alkyl bromides and mixtures thereof. The alkyllithium reactant may be used in the form of an ether or hydrocarbon solution thereof, but it is preferably used in the form of a hydrocarbon solution thereof. When a hydrocarbon solution of an isopropyl group-containing dialkylmagnesium compound according to the present invention is prepared, at least one of the alkyl halide reactant and the alkyllithium reactant should include at least one compound containing an isopropyl group. As the other alkyl group than the isopropyl group, there can be mentioned a n-butyl group, a n-propyl group and an ethyl group, and a n-butyl group is preferred from the viewpoint of viscosity of a hydrocarbon solution to be formed. Preferred combinations of the alkyl halide reactant and the alkyllithium reactant are isopropyl chloride-n-butyllithium, n-butyl chloride-isopropyllithium, isopropyl chloride-n-propyllithium, isopropyl bromide-ethyllithium, n-propyl bromide-isopropyllithium and metallic magnesium (for example, n-butyl chloride is first dropped into the reaction system to effect the reaction with Mg and isopropyl bromide is then dropped into the reaction system) or a method in which a mixture of two or more kinds of alkyl halides is subjected to a reaction with metallic magnesium (for example, a mixture of n-butyl chloride and isopropyl bromide is dropped into the reaction system and reacted with Mg). The latter method is especially preferred. The molar ratio of the reactants is such that the amount of magnesium to be used is larger than, preferably 10 to 30% in excess of, the equimolar amount with the total amount of the alkyl halides. The mixing molar ratio of the isopropyl halide: at least one other specified alkyl halide may be 0.4:1.6 to 1.6:0.4, preferably 0.9:1.1 to 1.1:0.9, especially preferably 1:1. The reaction temperature and the reaction time are not particularly critical, but it is preferred that the reaction be carried out at the reflux temperature of the solvent and continued at least for 30 minutes.

In the hydrocarbon solution of the isopropyl group-containing dialkylmagnesium compound prepared according to the process (c), the residual halogen values are not substantially detected. Since no ether is used in the process (c), no ether is contained in the hydrocarbon solution obtained according to the process (c).

The present invention will now be described in detail with reference to the following Examples that by no means limit the scope of the invention.

EXAMPLE 1

(1) Preparation of Ether Solution of (iso-$C_3H_7$)MgCl:

Under an atmosphere of nitrogen, a 300 cc flask equipped with a water-cooling reflux tube was charged with 8 g (0.33 g-atom) of powdery magnesium, 250 ml of dehydrated and refined diethyl ether and a small piece of iodine, and 22.6 ml (0.25 mol) of dehydrated and refined isopropyl chloride was added dropwise to the charged mixture from a dropping funnel over a period of 1 hour while refluxing the mixture on an oil bath maintained at 35° to 45° C. In the course of the dropwise addition, the brown color of the mixture due to iodine disappeared, and the reaction began. After termination of the dropwise addition, the mixture was stirred under reflux for another 1 hour to complete the reaction. The slurry obtained was filtered under an atmosphere of nitrogen to obtain a colorless transparent ether solution of (iso-$C_3H_7$)MgCl. The solution was analyzed to find that the Mg concentration was 0.90 mol/liter as determined according to the chelate titration method and the Cl concentration was 0.91 mol/liter as determined according to the Volhard method.

(2) Preparation of Hexane Solution of (iso-$C_3H_7$)Mg(n-$C_4H_9$):

A distillation apparatus was assembled, and a 400 cc flask of the distillation apparatus was charged with 130 ml of the ether solution prepared in (1) above and having a Mg concentration of 0.90 mol/liter [117 millimols of (iso-$C_3H_7$)MgCl]. 65 ml of a n-hexane solution having a n-$C_4H_9$Li concentration of 1.80 mols/liter (117 millimols of n-$C_4H_9$Li) was gradually poured into the ether solution under agitation by using a syringe. Upon pouring the n-hexane solution into the ether solution, a large amount of a fine white precipitate of LiCl was formed. Then, 80 ml of dehydrated n-hexane was added to the reaction mixture, and the resulting mixture was heated on an oil bath to effect distillation. At about 35° C., distillation of the ether started. After 80 ml of the distillate had been distilled off, 100 ml of n-hexane was added to the remaining mixture and 100 ml of the distillate was distilled off. Then, 150 ml of n-hexane was further added to the remaining mixture and 215 ml of the distillate was distilled off. By such distillation, the ether was substantially completely distilled off, and the distillation temperature rose to 68°-70° C. which is the boiling point of n-hexane. The heating was stopped, and the resulting white slurry in the flask was transferred into a glass vessel under an atmosphere of nitrogen and allowed to stand still for 1 day. The precipitate of LiCl settled in the bottom portion of the vessel. The supernatant was taken out under an atmosphere of nitrogen to obtain a light-yellow transparent n-hexane solution of (iso-$C_3H_7$)Mg(n-$C_4H_9$). The solution was analyzed to find that the Mg concentration was 0.80 mol/liter as determined according to the chelate titration method, the residual Cl concentration was lower than 0.01 mol/liter as determined according to the Volhard method, and the residual ether concentration was lower than 0.05 weight % as determined by gas chromatography. Hydrolysis of the solution produced a mixed gas having a propane/n-butane molar ratio of 1.00/1.01 as determined by gas chromatography.

The yield of (iso-$C_3H_7$)Mg(n-$C_4H_9$) based on the starting isopropyl chloride was 80%.

EXAMPLES 2 to 9

The preparation of solutions was carried out by using starting materials as listed in Table 1 is substantially the same manner as described in Example 1. The results obtained are shown in Table 1.

TABLE 1

| | Starting Materials | | Product (Hexane Solution) | | | |
|---|---|---|---|---|---|---|
| Example No. | R'X | R"Li | Chemical Formula | Mg (mol/liter) | Halogen (mol/liter) | Ether (wt %) |
| 1 | iso-$C_3H_7$Cl | n-$C_4H_9$Li | (iso-$C_3H_7$)Mg(n-$C_4H_9$) | 0.80 | below 0.01 | below 0.05 |
| 2 | iso-$C_3H_7$Cl | 0.4/0.6 mixture of n-$C_4H_9$Li and iso-$C_3H_7$Li | (iso-$C_3H_7$)$_{1.6}$Mg(n-$C_4H_9$)$_{0.4}$ | 0.50 | below 0.01 | below 0.05 |
| 3 | iso-$C_3H_7$Cl | 0.9/0.1 mixture of n-$C_4H_9$Li and iso-$C_3H_7$Li | (iso-$C_3H_7$)$_{1.1}$Mg(n-$C_4H_9$)$_{0.9}$ | 0.70 | below 0.01 | below 0.05 |
| 4 | 0.9/0.1 mixture of iso-$C_3H_7$Cl and n-$C_4H_9$Cl | n-$C_4H_9$Li | (iso-$C_3H_7$)$_{0.9}$Mg(n-$C_4H_7$)$_{1.1}$ | 0.72 | below 0.01 | below 0.05 |
| 5 | 0.4/0.6 mixture of iso-$C_3H_7$Cl and n-$C_4H_9$Cl | n-$C_4H_9$Li | (iso-$C_3H_7$)$_{0.4}$Mg(n-$C_4H_9$)$_{1.6}$ | 0.55 | below 0.01 | below 0.05 |
| 6 | iso-$C_3H_7$Br | n-$C_4H_9$Li | (iso-$C_3H_7$)Mg(n- | 0.85 | below 0.01 | below 0.05 | mixtures thereof. Especially preferred are isopropyl chloride-n-butyllithium, n-butyl chloride-isopropyllithium and mixtures thereof.

The reaction procedures are now described by way of example.

The first stage reaction is an ordinary reaction for the synthesis of Grignard reagents, and it is carried out in an ether solvent. As the ether solvent to be used, there can be mentioned, for example, diethyl ether, tetrahydrofuran, di-n-butyl ether, dioxane and mixtures thereof. From the viewpoint of easiness in the solvent substitution to be carried out later, it is most preferred to use diethyl ether which has a low boiling point. A mixture of an ether and a hydrocarbon may be used as the solvent, but, in this case, it is recommended that the ether should be used at least in an equimolar amount to that of the compound R'MgX to be formed, especially in an amount of at least 2 mols per mol of the compound R'MgX. The reaction is preferably carried out under reflux of the solvent while dropwise adding the alkyl halide reactant to a mixture of metallic magnesium and the solvent according to customary procedures. The reaction is preferably continued at least for 30 minutes. After completion of the reaction, the ether solution of the Grignard reagent is obtained by filtration or decantation of the formed slurry in which the solids are the unreacted magnesium and a small amount of the magnesium halide.

In the second stage reaction, the ether solution of the Grignard reagent (R'MgX) synthesized in the first stage reaction is subjected to a reaction with the alkyllithium reactant (R"Li) and the solvent substitution is carried out to obtain a hydrocarbon solution of an isopropyl group-containing dialkylmagnesium compound. In this reaction, it is preferred that the R'MgX/R"Li molar ratio be about 1/1. When the amount of the alkyllithium reactant (R"Li) is insufficient, a part of halogen values remains in the form of R'MgX in the resulting solution and the R'MgX is solvated by the ether, often leading to some difficulty in removing ether completely by the solvent substitution. The reaction temperature is not particularly critical, but the reaction is usually carried out at temperatures ranging from room temperature to 200° C. The reaction time is not particularly critical, but the reaction is usually continued at least for 30 minutes. The solvent substitution may be carried out according to either a method (I) or a method (II) given below. In the method (I), a hydrocarbon solvent is added to a white slurry which has been obtained by dropwise adding the alkyllithium reactant (R"Li) to the ether solution of R'MgX, and the ether is removed by distillation. In the method (II), a hydrocarbon solvent is added to the ether solution of R'MgX and the ether is removed by distillation, followed by dropwise adding the alkyllithium reactant (R"Li) to the resultant to effect the second stage reaction. For effecting better removal of the ether and halogen values, the method (I) is preferred. As the hydrocarbon solvent that is used for the solvent substitution, there can be mentioned, for example, aliphatic hydrocarbons such as n-pentane, isopentane, n-hexane, n-heptane, n-octane, iso-octane, and pentamethylheptane; cycloaliphatic hydrocarbons such as cyclohexane, methylcyclohexane, methylcyclopentane, cycloheptane, and cyclooctane; and aromatic hydrocarbons such as benzene, toluene, xylenes, ethylbenzene, and α-methylnaphthalene. They may be used either alone or in mixture. Aliphatic hydrocarbons, cycloaliphatic hydrocarbons and mixtures thereof are preferred. After completion of the solvent substitution, the slurry containing the solid lithium halide is subjected to filtration or decantation to obtain a hydrocarbon solution of an isopropyl group-containing dialkylmagnesium compound (R'MgR") according to the present invention.

The residual halogen values and residual ether are not substantially detected in the so obtained hydrocarbon solution of the isopropyl group-containing dialkylmagnesium compound.

Process (a'):

The process (a') is different from the process (a) in that an ether is not used at all and all the reactions are carried out in a hydrocarbon solvent.

The same starting materials as used in the process (a) can be used in this process (a'). A fine powder of metallic magnesium of about 100 mesh in size, which has been activated with iodine or by washing with an organometallic compound according to a known method, is preferably used as the starting magnesium. The alkyllithium is used in the form of a hydrocarbon solution thereof. As the preferred combination of the starting alkyl halide and alkyllithium to be used in the process (a'), there can be mentioned n-butyl chloride-isopropyllithium and ethyl bromide-isopropyllithium, and a combination of n-butyl chloride-isopropyllithium is especially preferred.

As described before, in the process (a'), an ether solvent is not used at all and all the reactions are carried out in a hydrocarbon solvent. A compound of the R'MgX type formed by the first stage reaction is a solid insoluble in the hydrocarbon reaction medium. In the second stage reaction, this solid compound is reacted with the alkyllithium in the hydrocarbon solvent to obtain a hydrocarbon solution of an isopropyl group-containing dialkylmagnesium compound according to the present invention. In the process (a'), since no ether is used, the solvent substitution as described before with respect to the process (a) is not needed. The molar ratio of the reactants, the reaction temperature and the reaction time are substantially the same as those employed in the process (a).

Also in the hydrocarbon solution of the isopropyl group-containing dialkylmagnesium compound obtained according to the process (a'), the residual halogen values are not substantially detected. Of course, no ether is contained in the solution because no ether is used throughout the reactions.

Process (c):

The process (c) is a direct synthesis process without use of an alkyllithium reactant in which process metallic magnesium is, in a hydrocarbon solvent, reacted with a mixed alkyl halide reactant of an isopropyl halide and at least one other alkyl halide having an alkyl group selected from n-$C_4H_9$, n-$C_3H_7$ and $C_2H_5$.

The starting materials to be used in the process (c) are as follows. The same metallic magnesium as preferably used in the process (a') is also preferred in the process (c). As the preferred combination of the starting materials constituting the mixed alkyl halide reactant, there can be mentioned, for example, n-butyl chloride-isopropyl bromide, n-propyl bromide-isopropyl bromide and n-butyl bromide-isopropyl chloride. A combination of n-butyl chloride-isopropyl bromide is especially preferred.

For effecting the reaction involved in the process (c), there may be adopted either a method in which two or more kinds of alkyl halides are reacted in sequence with TABLE 1-continued

| Example No. | Starting Materials R'X | R"Li | Product (Hexane Solution) Chemical Formula | Mg(mol/liter) | Halogen (mol/liter) | Ether (wt %) |
|---|---|---|---|---|---|---|
| 7 | n-$C_4H_9Cl$ | iso-$C_3H_7Li$ | (iso-$C_3H_7$)Mg(n-$C_4H_9$) | 0.75 | below 0.01 | below 0.05 |
| 8 | iso-$C_3H_7Cl$ | n-$C_3H_7Li$ | (iso-$C_3H_7$)Mg(n-$C_3H_7$) | 0.73 | below 0.01 | below 0.05 |
| 9 | iso-$C_3H_7Cl$ | $C_2H_5Li$ | (iso-$C_3H_7$)Mg($C_2H_5$) | 0.63 | below 0.01 | below 0.05 |

Note:
The ratios described in Table 1 with respect to the mixtures of starting materials are on a molar basis.

EXAMPLE 10

The preparation of a solution was carried out in substantially the same manner as described in Example 1 except that methylcyclohexane was used instead of n-hexane, to obtain a methylcyclohexane solution of (iso-$C_3H_7$)Mg(n-$C_4H_9$). The analysis results were the same as those obtained in Example 1.

EXAMPLE 11

(1) Synthesis of (n-$C_4H_9$)MgCl Solid in Hydrocarbon:

Under an atmosphere of nitrogen, 6.1 g (0.25 g-atom) of a 100–200 mesh powder of metallic magnesium, 185 ml of dehydrated and refined n-heptane and a small piece of iodine were charged into a 300 cc flask equipped with a water-cooling reflux tube. 0.25 ml of dehydrated and refined n-butyl chloride was added dropwise to the charged mixture from a dropping funnel over a period of 1 hour while refluxing the mixture on an oil bath maintained at 100° C. In the course of the dropwise addition, the reddish purple color of the mixture due to iodine disappeared and the reaction started. After completion of the dropwise addition, the mixture was agitated for 2 hours under reflux to complete the reaction. A gray mud-like slurry was obtained. This slurry was analyzed to find that 0.25 mol of (n-$C_4H_9$)MgCl was contained in the solids of the slurry and the liquid portion was free of magnesium values.

(2) Preparation of Heptane Solution of (iso-$C_3H_7$)Mg(n-$C_4H_9$):

Under an atmosphere of nitrogen, 117 millimols (based on Mg) of the n-heptane slurry containing the (n-$C_4H_9$)MgCl solid, which was prepared in (1) above, was charged into a 400 cc flask, and a n-heptane solution containing 117 millimols of iso-$C_3H_7$Li was gradually added dropwise to the slurry at 100° C. under reflux and agitation. After completion of the dropwise addition, the mixture was stirred at 100° C. for 2 hours. Then, the heating was stopped and the slurry was filtered under an atmosphere of nitrogen to obtain a n-heptane solution of (iso-$C_3H_7$)Mg(n-$C_4H_9$). The solution was analyzed to find that the Mg concentration was 0.82 mol/liter and the residual Cl concentration was lower than 0.01 mol/liter. In this Example, no ether was used, and, hence, the solution obtained contained no ether.

EXAMPLE 12

A n-heptane solution of (iso-$C_3H_7$)$_{0.4}$Mg(n-$C_4H_9$)$_{1.6}$ was prepared in substantially the same manner as described in Example 11 except that a 0.6/0.4(molar ratio) mixture of n-$C_4H_9Li$ and iso-$C_3H_7Li$ was used instead of iso-$C_3H_7Li$. The solution was analyzed to find that the Mg concentration was 0.55 mol/liter and the residual Cl concentration was lower than 0.01 mol/liter. In this Example, no ether was used, and, hence, the solution obtained contained no ether.

EXAMPLE 13

In this Example, the direct synthesis of (iso-$C_3H_7$)Mg(n-$C_4H_9$) in a hydrocarbon solvent is illustrated.

Under an atmosphere of nitrogen, 8 g (0.33 g-atom) of a 100–200 mesh powder of metallic magnesium, 185 ml of dehydrated and refined n-heptane and a small piece of iodine were charged into a 300 cc flask equipped with a water-cooling reflux tube. 0.25 mol of a 0.5/0.5 (molar ratio) mixture of dehydrated and refined iso-$C_3H_7Br$ and n-$C_4H_9Cl$ was added dropwise to the charged mixture from a dropping funnel over a period of 1 hour while refluxing the mixture on an oil bath maintained at 100° C. In the course of the dropwise addition, the reddish purple color of the mixture due to iodine disappeared and the reaction started. After completion of the dropwise addition, the mixture was stirred under reflux for 2 hours to complete the reaction. A gray mud-like slurry was obtained. The slurry was filtered under an atmosphere of nitrogen to obtain a n-heptane solution of (iso-$C_3H_7$)Mg(n-$C_4H_9$). The solution was analyzed to find that the Mg concentration was 0.20 mol/liter and the total concentration of residual Cl and Br was lower than 0.01 mol/liter. In this Example, no ether was used, and, hence, the solution obtained contained no ether.

EXAMPLES 14 to 17

The preparation of solutions was carried out by using starting materials as listed in Table 2 in substantially the same manner as described in Example 13. The results obtained are shown in Table 2.

TABLE 2

| Example No. | Starting Materials (R'X + R"X) | Product (Heptane Solution) Chemical Formula | Mg(mol/liter) | Halogen (mol/liter) |
|---|---|---|---|---|
| 13 | 0.5/0.5 mixture of iso-$C_3H_7Br$ and n-$C_4H_9Cl$ | (iso-$C_3H_7$)Mg(n-$C_4H_9$) | 0.20 | below 0.01 |
| 14 | 0.8/0.2 mixture of iso-$C_3H_7Br$ and n-$C_4H_9Cl$ | (iso-$C_3H_7$)$_{1.6}$Mg(n-$C_4H_9$)$_{0.4}$ | 0.12 | below 0.01 |
| 15 | 0.55/0.45 mixture of iso-$C_3H_7Br$ and n-$C_4H_9Cl$ | (iso-$C_3H_7$)$_{1.1}$Mg(n-$C_4H_9$)$_{0.9}$ | 0.17 | below 0.01 |
| 16 | 0.45/0.55 mixture of iso-$C_3H_7Br$ and n-$C_4H_9Cl$ | (iso-$C_3H_7$)$_{0.9}$Mg(n-$C_4H_9$)$_{1.1}$ | 0.19 | below 0.01 |

TABLE 2-continued

| Example No. | Starting Materials (R'X + R"X) | Product (Heptane Solution) | | |
|---|---|---|---|---|
| | | Chemical Formula | Mg(mol/liter) | Halogen (mol/liter) |
| 17 | 0.2/0.8 mixture of iso-$C_3H_7Br$ and n-$C_4H_9Cl$ | (iso-$C_3H_7$)$_{0.4}$Mg(n-$C_4H_9$)$_{1.6}$ | 0.14 | below 0.01 |

Note:
The ratios described with respect to the mixtures of starting materials are on a molar basis.

What is claimed is:

1. A hydrocarbon-soluble isopropylmagnesium compound having the general formula:

$$(iso\text{-}C_3H_7)_m MgR_{2-m}$$

wherein m is a number in the range of the formula $0.4 \leq m \leq 1.6$ and R represents a member selected from the group consisting of n-$C_4H_9$, n-$C_3H_7$, $C_2H_5$ and combinations thereof.

2. A compound according to claim 1, wherein m is in the range of the formula $0.9 \leq m \leq 1.1$.

3. A compound according to claim 2 wherein m is 1.

4. A compound according to any one of claims 1 to 3, wherein R is n-$C_4H_9$.

5. A hydrocarbon solution comprising:
(a) an isopropylmagnesium compound having the general formula:

$$(iso\text{-}C_3H_7)_m MgR_{2-m}$$

wherein m is a number in the range of the formula $0.4 \leq m \leq 1.6$ and R represents a member selected from the group consisting of n-$C_4H_9$, n-$C_3H_7$, $C_2H_5$ and combinations thereof; and (b) a solvent selected from the group consisting of aliphatic, cycloaliphatic and aromatic hydrocarbons, and mixtures thereof.

6. A hydrocarbon solution according to claim 5, wherein m is in the range of the formula $0.9 \leq m \leq 1.1$.

7. A hydrocarbon solution according to claim 6, wherein m is 1.

8. A hydrocarbon solution according to any one of claims 5 to 7, wherein R is n-$C_4H_9$.

9. A hydrocarbon solution according to any one of claims 5 to 8, wherein the solvent is selected from the group consisting of aliphatic and cycloaliphatic hydrocarbons, and mixtures thereof.

10. A hydrocarbon solution according to any one of claims 5 to 9, wherein the isopropylmagnesium compound concentration is at least 0.05 mol/liter.

* * * * *